(12) United States Patent
Fukui (10) Patent No.: US 8,501,100 B2
(45) Date of Patent: Aug. 6, 2013

(54) OXYGEN DETECTION USING METALLOPORPHYRINS

(75) Inventor: Toshimi Fukui, Ohtsu (JP)

(73) Assignee: Empire Technology Development LLC, Wilmington, DE (US)

( * ) Notice: Subject to any disclaimer, the term of this patent is extended or adjusted under 35 U.S.C. 154(b) by 95 days.

(21) Appl. No.: 13/000,796

(22) PCT Filed: Jun. 16, 2010

(86) PCT No.: PCT/US2010/038800
§ 371 (c)(1),
(2), (4) Date: Dec. 22, 2010

(87) PCT Pub. No.: WO2011/159291
PCT Pub. Date: Dec. 22, 2011

(65) Prior Publication Data
US 2011/0311987 A1     Dec. 22, 2011

(51) Int. Cl.
*G01N 21/00* (2006.01)

(52) U.S. Cl.
USPC ..... 422/82.09; 422/400; 422/420; 422/82.05; 422/83; 436/127; 436/136; 436/137; 436/138

(58) Field of Classification Search
USPC ...... 422/400, 420, 82.05, 82.09, 83; 436/127, 436/136, 137, 138
See application file for complete search history.

(56) References Cited

U.S. PATENT DOCUMENTS

| 4,781,889 A | 11/1988 | Fukasawa et al. |
| 5,359,681 A | 10/1994 | Jorgenson et al. |
| 2003/0235513 A1 | 12/2003 | Asai et al. |
| 2010/0045997 A1* | 2/2010 | Hong et al. .......... 356/445 |
| 2010/0166604 A1* | 7/2010 | Lim et al. .......... 422/57 |

FOREIGN PATENT DOCUMENTS

| JP | 2003-344382 | 12/2003 |
| WO | WO 2011/106057 | * 9/2011 |

OTHER PUBLICATIONS

International Search Report and Written Opinion for PCT/US2010/038800 mailed Aug. 4, 2010.
Sakai, H. et al., "Influence on Phagocytic Activity and Histopathological Changes in Reticuloendothelial System," American Journal of Pathology, vol. 159, No. 3, Sep. 2001, pp. 1079-1088.
Kano, K. et al., "A Myglobin Functional Model Composed of a Ferrous Porphyrin and a Cyclodextrin Dimer with an Imidazole Linker," Chem. Asian J., 2006, pp. 358-366.
http://www.waseda.jp/prj-artifblood/HbV-ja.html, retrieved Feb. 25, 2010, from online, 2 pages (English translation not available).
http://www.new-cosmos.co.jp/tec/sensor/index8.html, retrieved Feb. 25, 2010, from online, 1 page (English translation not available).

(Continued)

*Primary Examiner* — Monique Cole
(74) *Attorney, Agent, or Firm* — Foley & Lardner LLP (57) ABSTRACT

An oxygen sensor includes a metalloporphyrin for detecting oxygen levels. The oxygen sensors may also include a light source and a detector. The sensors are configured to measure changes in spectra in response to the redox reaction. They can detect a variety of samples for presence and changes in oxygen concentration in both solution and gaseous form.

13 Claims, 4 Drawing Sheets

OTHER PUBLICATIONS

Eguchi, T. et al., "Current status of development of solid-state oxygen sensors operating at ambient temperature," Faculty of Engineering, Science University of Tokyo, retrieved Feb. 25, 2010, from online, 15 pages (w/English abstract).

Yamada, Y., "Contribute to healthy living light Chapter 3," accessed at http://www.mext.go.jp/b_menu/shingi/gijyutu/gijyutu3/toushin/07091111/008.htm, accessed on May 17, 2012, 19 pages (English Translation).

Yoshio, A., "Light the importance of DNA analysis in the future (1)," accessed at http://square.umin.ac.jp/aoki530t/prorogu_daigaku/hikari.htm, accessed on May 17, 2012, 17 pages (English Translation).

* cited by examiner

OXYGEN DETECTION USING METALLOPORPHYRINS

CROSS-REFERENCE TO RELATED APPLICATIONS

The present application is a U.S. national stage application claiming the benefit of International Application No. PCT/US2010/038800, filed on Jun. 16, 2010, the entire contents of which is incorporated herein by reference in its entirety.

FIELD

The present technology is generally related to the field of sensors.

BACKGROUND

The following description is provided to assist the understanding of the reader. None of the information provided is admitted to be prior art.

Monitoring the concentration of oxygen in liquids and gases is required in many fields. For this reason, oxygen sensors or analyzers find a wide variety of applications. For example, biomedical applications use various types of oxygen sensors to detect and measure the oxygen content of liquid blood samples and physiological gas samples; chemical applications include manufacturing processes that require measurement of oxygen such as in the beer brewing process or during manufacture of dyes and paints, and environmental applications include monitoring oxygen levels in marine ecosystems, and in power plants.

Despite having a broad range of applications, oxygen analyzers and sensors that are currently available suffer from disadvantages such long detection times, low sensitivity, limited accuracy, limited life of the sensor and ability to detect oxygen selectively in one physical form or the other (i.e. either liquid or gaseous).

Porphyrins are macrocyclic molecular compounds having a ring-shaped tetrapyrrolic core which is capable of forming complexes with metal ions. Metalloporphyrins are complexes including various derivatives of porphyrins, generally in their dianionic form, coordinated to a metal ion. This coordination of a metal ion with a porphyrin nucleus leads to compounds which are analogous to several important biological compounds such as, but not limited to, hemoglobin, chlorophyll, cytochromes and the like.

SUMMARY

In one aspect, an oxygen sensor is provided including a substrate configured for spectral analysis including at least a partial coating of a metalloporphyrin that is configured to bind oxygen. In some embodiments, the porphyrin of the metalloporphyrin includes hemoglobin, hemerythrin, chlorocruorin, vanabin, pinnaglobin, myoglobin, erythrocruorin, neuroglobin, leghemoglobin, cytoglobin, red blood cells, or a mixture of any two or more such metalloporphyrins. In some embodiments, the metal of the metalloporphyrin is iron, vanadium, manganese, cobalt, nickel, copper, chromium, platinum, palladium, silver, or gold.

In some embodiments, the metalloporphyrin is in a state in which the metal may be oxygenated by molecular oxygen. In some embodiments, the metalloporphyrin includes a microbead or microcapsule. In some embodiments, the substrate includes a chamber, a tube, or a channel.

In some embodiments, the oxygen sensor also includes a detector for detecting a spectral profile. In some embodiments, the spectral profile is an emission spectrum or an absorption spectrum.

In some embodiments, the substrate includes quartz, glass, plastic, or a salt. In some such embodiments, the substrate is a salt including $CaF_2$ or $MgF_2$. In some embodiments, the oxygen sensor also includes an gas-permeable membrane.

In another aspect, an oxygen sensor is provided including, a chamber configured to permit spectral analysis; and a metalloporphyrin configured to bind oxygen and including a microbead or microcapsule. In some embodiments, the porphyrin of the metalloporphyrin includes hemoglobin, hemerythrin, chlorocruorin, vanabin, pinnaglobin, myoglobin, erythrocruorin, neuroglobin, leghemoglobin, cytoglobin, red blood cells, or a mixture of any two or more such porphyrins. In some embodiments, the metal of the metalloporphyrin is iron, vanadium, manganese, cobalt, nickel, copper, chromium, platinum, palladium, silver, or gold.

In some embodiments, the metalloporphyrin is in a state in which it is configured to bind oxygen. In some embodiments, the metalloporphyrin includes a microbead or microcapsule. In some embodiments, the substrate includes a chamber, a tube, or a channel.

In some embodiments, the oxygen sensor also includes a detector for detecting a spectral profile. In some embodiments, the spectral profile is an emission spectrum or an absorption spectrum.

In some embodiments, the substrate includes quartz, glass, plastic, or a salt. In some such embodiments, the substrate is a salt including $CaF_2$ or $MgF_2$. In some embodiments, the oxygen sensor also includes an gas-permeable membrane.

In another aspect, an apparatus is provided for measuring the oxygen content of a sample including: a substrate at least partially coated with a metalloporphyrin configured to bind oxygen; a light source configured to illuminate the substrate; and a detector configured to receive light from the substrate. In some embodiments, the light source emits ultraviolet light, visible light, near infrared light, infrared light, or far infrared light. In some embodiments, the substrate further includes an gas-permeable membrane. In some embodiments, the substrate is transparent. In some embodiments, the substrate does not absorb infrared, ultraviolet or visible light at a monitored wavelength.

In some embodiments, the substrate includes quartz, glass, plastic, or a salt. In some such embodiments, the substrate is a salt including $CaF_2$ or $MgF_2$.

In some embodiments, the metalloporphyrin includes microcapsules or microbeads. In some embodiments, the metalloporphyrin is in a state in which it may bind oxygen. For example, it may be in a state in which the metal of the metalloporphyrin may bind oxygen ($O_2$). In some embodiments, the substrate is configured to allow for the sample to be contacted with the metalloporphyrin. In some embodiments, the sample includes a liquid phase or gaseous phase.

In some embodiments, the porphyrin of the metalloporphyrin includes hemoglobin, hemerythrin, chlorocruorin, vanabin, pinnaglobin, myoglobin, or red blood cells. In some embodiments, the metal of the metalloporphyrin is iron, vanadium, manganese, cobalt, nickel, copper, chromium, platinum, palladium, silver and gold.

In some embodiments, the detector is configured to detect an oxygen content of the sample by detecting a spectral profile. In some such embodiments, the spectral profile is an emission spectrum or an absorption spectrum.

In another aspect, a method is provided for detecting oxygen gas or dissolved oxygen gas in a sample, the method including: introducing the sample to an oxygen sensor including: a chamber including a substrate at least partially coated with a metalloporphyrin configured to bind oxygen; a light source; and a detector; contacting the metalloporphyrin with the sample; illuminating the chamber and sample with the light source; and detecting a spectral profile of the light source before and after introducing the sample. In some embodiments, the method includes observing a change in the spectral profile of the chamber after introducing the sample. In some such embodiments, the spectral profile is an absorption spectrum or an emission spectrum. In some embodiments, the metalloporphyrin is in a deoxygenated state in which it may bind oxygen, prior to introducing the sample, and at least a portion of the metalloporphyrin is bound to the oxygen after introducing the sample (i.e. an oxygenated state).

In another aspect, a method is provided for detecting the oxygen gas or dissolved oxygen gas content of a sample, the method including: contacting the sample and a metalloporphyrin configured to bind oxygen in an oxygen sensor including: a chamber; a light source; and a detector; illuminating the chamber and sample with the light source; and detecting a spectral profile of the sample before and after introducing the sample; where the metalloporphyrin includes a microbead or microcapsule, or is retained in a clathrate compound.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Generally, provided herein are oxygen sensors, devices, apparatuses, and methods of use of such sensors, devices, and apparatuses. The oxygen sensors utilize a metalloporphyrin that is configured to bind oxygen to determine either the presence of oxygen in a sample and/or an oxygen concentration in a sample. The determination is generally performed using spectral analysis of the sample in the presence of the metalloporphyrin.

In one aspect, an oxygen sensor is provided which includes a substrate configured to permit analysis and includes at least a partial coating of a metalloporphyrin where the metalloporphyrin is configured to bind oxygen.

Metalloporphyrins encompass complexes including various derivatives of porphyrins coordinated to a metal ion. Any suitable porphyrin having oxygen-binding capability can be used to complex with the metal ion. Such porphyrin complexes may be of natural origin or may be produced by synthetic methods. Thus, in one embodiment, the porphyrin of the metalloporphyrin may include, but is not limited to, hemoglobin, hemerythrin, chlorocruorin, vanabin, pinnaglobin, myoglobin, erythrocruorin, neuroglobin, leghemoglobin, cytoglobin, red blood cells, or a mixture of any two or more thereof. The metal of the metalloporphyrin can be any suitable metal capable of forming a complex with the porphyrin derivatives, and which is capable of binding oxygen, such that upon contact with oxygen gas, or dissolved oxygen gas in a solution, the metal becomes oxygenated.

The metal ion of the metalloporphyrin may be in a formally reduced oxidation state (i.e. having a formal negative charge), or it may be in a formally oxidized oxidation state (i.e. having a formal positive charge) but which is subject to further oxidation by oxygen gas, or dissolved oxygen gas. The metal should be in an oxidation state in which the metal will bind oxygen.

Accordingly, in some embodiments, the metal of the metalloporphyrin may be, but is not limited to, iron, vanadium, manganese, cobalt, nickel, copper, chromium, platinum, palladium, silver, or gold. In illustrative embodiments, e.g., iron-containing metalloporphyrins include hemoglobin, hemerithrin, chlorocruorin, and myoglobin, vanadium-containing metalloporphyrin derivatives include vanabins, and manganese-containing derivatives include pinnaglobin.

In the oxygen sensor, the metalloporphyrins may be configured to bind oxygen. This can be achieved by maintaining the metalloporphyrin in a deoxygenated state prior to analysis, such that in the presence of oxygen, the metalloporphyrin binds the oxygen. The metalloporphyrins can be deoxygenated by any known method such as photochemical or radiation chemical methods, or by using saturated carbon dioxide or deoxygenated water. Thus, in certain illustrative embodiments, the metalloporphyrin may be contacted with saturated carbon dioxide solution or deoxidized water prior to exposure to a sample for analysis, resulting in deoxygenation of the metalloporphyrin. In some embodiments, the oxidation state of the metalloporphyrin complex may be adjusted prior to its use for oxygen detection. Therefore, in one embodiment, the metalloporphyrin may be in a formally reduced oxidation state. In other embodiments, the metalloporphyrin is in a formally oxidized oxidation state The metalloporphyrin compounds may be used as such, as a solution, or may be formulated into other forms. Thus, in one embodiment, the metalloporphyrin may be present in the form of a microbead or microcapsule. For example, in an illustrative embodiment, the metalloporphyrin complex may be encapsulated within a phospholipid bilayer membrane. Such encapsulation may be achieved e.g. by using phospholipid vesicles made by mixing high-purity metalloporphyrin and a lipid bilayer composed of suitable phospholipids e.g. Presome PPG-I. The mixture can be stirred at an appropriate temperature for a suitable period of time and the resulting multilamellar vesicles can be extruded through suitable membrane filters. The vesicle surface may be further modified with poly(ethylene glycol) to improve its mechanical and structural properties.

In other illustrative embodiments, the metalloporphyrin may be retained by a clathrate compound. In one example, a cyclodextrin dimer as a clathrate may be used to retain the metalloporphyrin complex. Such a cyclodextrin dimer may be prepared e.g. by forming a 1:1 inclusion complex of 5,10, 15,20-tetrakis-(4-sulfonatophenyl) porphinatoiron (II) ($Fe^{II}P$) and an O-methylated β-cyclodextrin dimer with an imidazole linker (ImCD).

As described above, the oxygen sensor includes a substrate configured to permit analysis. The substrate can be in any suitable physical form, shape or geometry which facilitates analysis. Thus, in one embodiment, the substrate may include a flat panel, a chamber, a receiver cell, a tube, or a channel among other configurations used during spectral analysis of a sample. In an illustrative embodiment, the substrate is a flat panel, such as e.g. a glass slide. The substrate can be made of any suitable material known in the art which is durable and which permits analysis of the oxygen content. In some embodiments, the substrate includes any material which permits a light emitted from a light source or an electromagnetic radiation to pass through. The substrate should not produce spectroscopic background noise that interferes or blocks observation of spectral regions of the sample and metalloporphyrin that will be monitored to determine the presence and/or concentration of oxygen in the sample. In some embodiments, the substrate may include quartz, glass, plastic, or a salt. In other embodiments, the substrate may be a salt including $CaF_2$ or $MgF_2$.

In some embodiments, the substrate is at least partially coated with a metalloporphyrin. In other embodiments, the substrate may be completely coated with metalloporphyrin. The substrate may be coated with the metalloporphyrin by suitable methods such as but not limited to, adsorption, chemical bonding, ion-exchange or electrochemical polymerization. In some embodiments, a thin film of metalloporphyrin may be used to coat the substrate. In other embodiments, the metalloporphyrin may be attached to a microbead, or encapsulated in a microcapsule or a clathrate complex and then fixed on to the substrate. Microbeads may include MACS® beads (available from Miltenyi Biotech). Thus, in some embodiments, the microbeads or microcapsules or clathrate complexes including metalloporphyrin may be fixed to the substrate using suitable fixing agents, including but not limited to non-aqueous resins such as, e.g., an acrylic, urethane, or epoxy-type resin. In certain embodiments, polymerizable materials or fixing agents may be applied to the substrate and the microcapsules or microbeads including metalloporphyrin may be fixed thereto using methods such as photo-curing or heat-curing methods.

The oxygen sensor may be configured to permit analysis of the oxygen content of both gaseous and liquid samples. In one aspect, the analysis is a spectral analysis. As the metalloporphyrin binds the oxygen, an absorption spectrum or an emission spectrum changes in response to the amount of metalloporphyrin-oxygen complex in the sample. Thus, the oxygen sensor may further include a detector for detecting a spectral profile. In some embodiments, the spectral profile may be an absorption or an emission. It is noted that while a transmission spectrum may be monitored, this is the same experiment as the determination of an absorption spectrum, with the data presented inversely.

Figure 1:
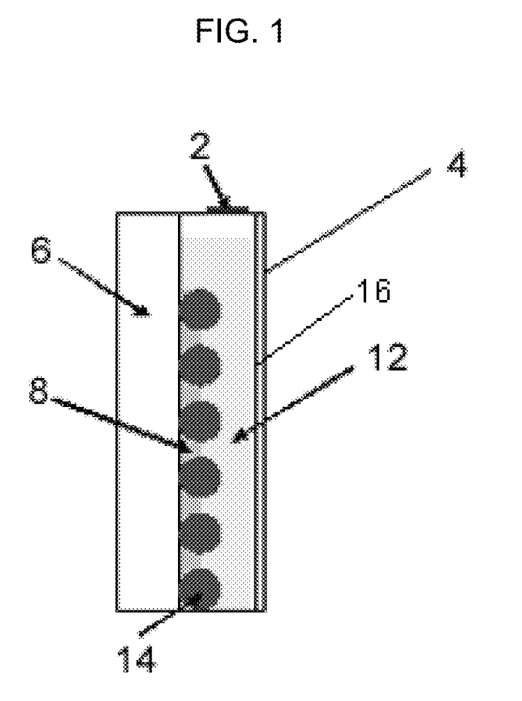
FIG. 1 is an illustration of an oxygen sensor, where a metalloporphyrin is sequestered on a substrate, according to one embodiment.

In one embodiment, the oxygen sensor is as illustrated in FIG. 1. As shown in FIG. 1, a metalloporphyrin 14 may be coated onto a substrate 6. In some embodiments, the substrate is partially coated, and in other embodiments, densely coated, the only limitation being that there is sufficient metalloporphyrin to capture the oxygen in a sample. A fixing agent 8 may also be used to assist in the coating. The metalloporphyrin 14 may optionally be within a microcapsule, and maintained in a deoxygenated state. Maintaining the metalloporphyrin a deoxygenated may be facilitated using deoxygenated water or carbon dioxide saturated water 12. The sample to be detected can be introduced via an inlet 2 in the substrate. Gaseous samples may also be introduced through a gas permeable (i.e. oxygen permeable) membrane 16.

The substrate may further be configured to permit the analysis of both liquid and gaseous samples. As such, the substrate may include an inlet to permit liquid and gaseous samples to be introduced. Where the substrate is configured to permit analysis of liquid samples, the substrate may either be coated with the metalloporphyrin, or an encapsulated metalloporphyrin may be introduced to the sample for analysis.

In embodiments where the substrate is configured to permit analysis of gaseous samples, the metalloporphyrin is coated on the substrate and the gaseous sample is introduced and contacted with the metalloporphyrin. In some embodiments, the sensor may include a gas-permeable membrane separating the metalloporphyrin and the sample, but which allows for oxygen in the sample to migrate across the membrane to the metalloporphyrin. The membrane also prevents the metalloporphyrin, or other reagents with the metalloporphyrin to migrate across the membrane to the sample. Gas permeable membranes may be made of any synthetic inert solid polymeric material such as, but not limited to, polytetrafluoroethylene (PTFE or Teflon), polysulfone, polyacrylonitrile, polyethylene terephthalate, polybuytlene terephthalate, polycarbonate, polyurethane, nylon-66, nylon-6, cellulose acetate, silicone rubber, cellophane, latex rubber, polyethylene and polypropylene, mixtures or blends of any two or more thereof, and the like. In an illustrative embodiment, the gas-permeable membrane includes Teflon. Regardless of the material used, the membrane should be permeable to oxygen and have the necessary mechanical strength. On example of a permeable membrane is set forth in U.S. Pat. No. 4,781,889 which discloses a nanoporous hollow fiber membrane. The mechanical strength may be imparted by the physical dimensions of such a membrane. In some embodiments, the permeable membranes has a thickness of from 5 μm to 80 μm, or from 10 μm to 30 μm. According to some embodiments, the permeable membrane has a pore size of from 0.01 μm to 5 μm, or from 0.01 μm to 2 μm.

Figure 2:
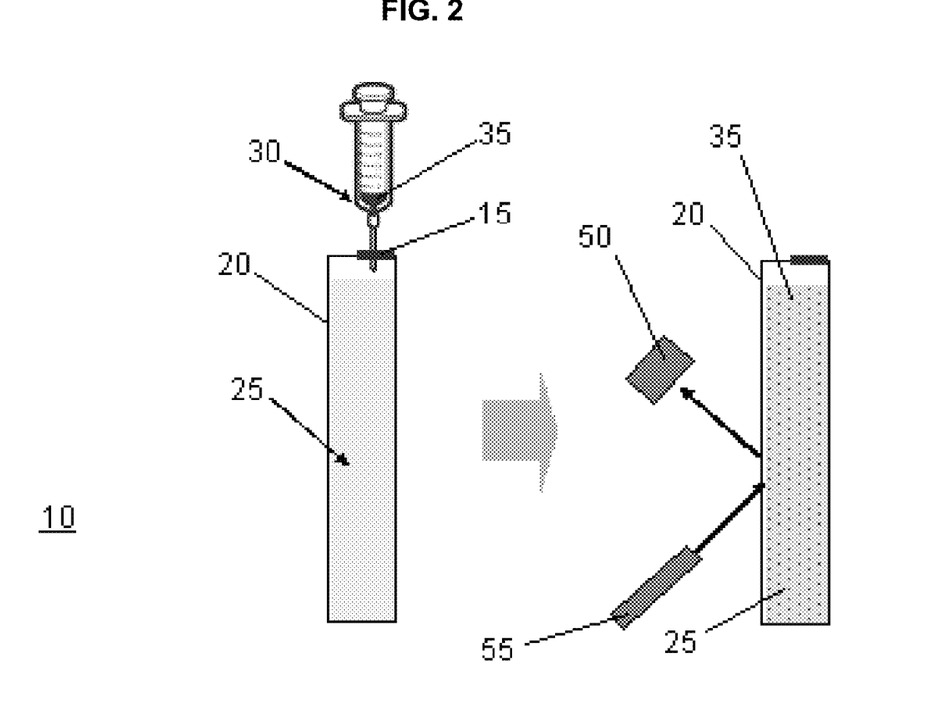
FIG. 2 is an illustration of an oxygen sensor, for analyzing the oxygen content in gaseous or liquid samples, according to one embodiment.

In another aspect, an oxygen sensor is provided which includes a chamber configured to permit analysis and a metalloporphyrin configured to bind oxygen. The metalloporphyrin compounds may be used as such, as a solution, or may be formulated into another, optionally more stable, form. Thus, in one embodiment, the metalloporphyrin may be present in the form of a microbead or microcapsule. In other embodiments, the metalloporphyrin may be retained by a clathrate compound. One embodiment of such a sensor is illustrated in FIG. 2. As seen in the figure, the apparatus includes a chamber 20 holding either the sample to be analyzed, or the metalloporphyrin, in a deoxygenated state 25 and having an inlet 15 from where the sample, or metalloporphyrin in a deoxygenated state 35 can be introduced via syringe 30, or other injection device. The sample or metalloporphyrin can be introduced into the chamber either manually or automatically. A syringe 30 is merely illustrated for simplicity, however the injection mechanism may be any such device known in the art. In some embodiments, the injector is calibrated to allow for the injection of a known amount of metalloporphyrin 35. The sensor also optionally includes a light source 55 and a detector 50.

The chamber can be in any suitable physical form, shape or geometry which facilitates analysis. Thus, in one embodiment, the chamber may include a chamber, a receiver cell, a tube, or a channel. The chamber can be made of any suitable material known in the art which permits analysis of the oxygen content. In some embodiments, the chamber includes any material which permits light from a light source or electromagnetic radiation to pass through. In one embodiment, the chamber may include quartz, glass, plastic, or a salt. In some embodiments, the chamber may be made of a salt such as $CaF_2$ or $MgF_2$, or other salt that is non-absorbing in a region of the electromagnetic spectrum at which a spectral analysis may be performed.

In some embodiments, the chamber is configured to be isolated from air, so that air does not enter the chamber and inadvertently oxygenate the metalloporphyrin. Thus, a gas permeable cover or septum may be included with the chamber, covering or preventing open access to an interior of the chamber.

Figure 3:
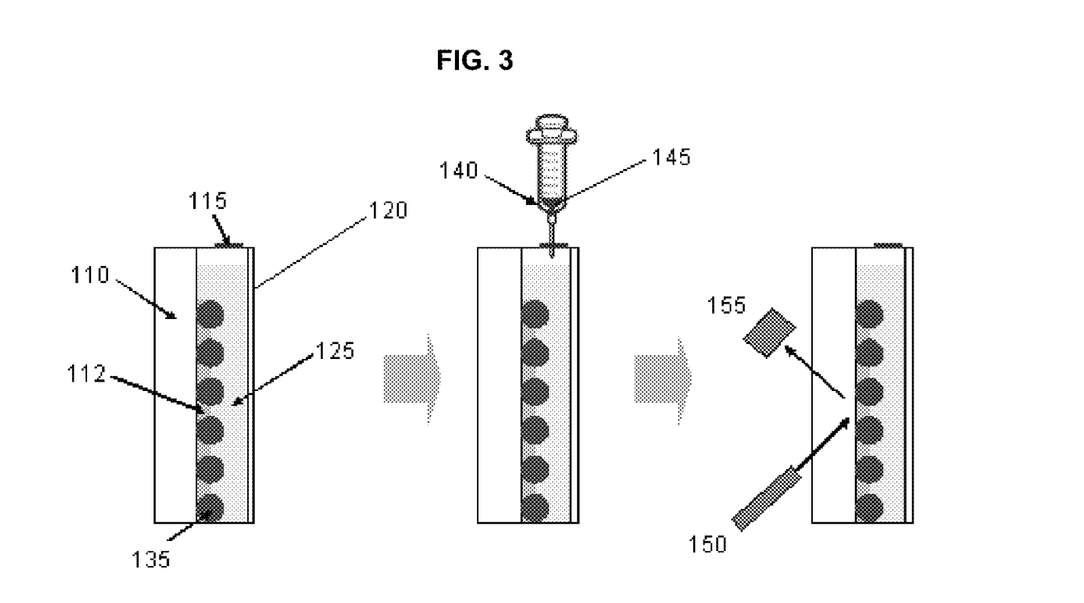
FIG. 3 is an illustration of an oxygen sensor for detecting oxygen in a sample, where a metalloporphyrin is sequestered on a substrate, according to one embodiment.

In another aspect, an apparatus is provided for measuring the oxygen content of a sample. In some embodiments, the apparatus includes a substrate at least partially coated with a metalloporphyrin; a light source configured to illuminate the substrate; and a detector configured to receive light from the substrate. In one embodiment, an illustrative apparatus is as illustrated in FIG. 3. As shown in FIG. 3, a metalloporphyrin 135 may be coated onto a substrate 110. As illustrated, a fixing agent 112 may also be used to assist in the coating. As shown, the metalloporphyrin 135 may optionally be within a microcapsule, and maintained in a deoxygenated state. The sample 145 to be detected can be introduced via an inlet 115 in the substrate using a sample injector 140. As stated above, the injector is illustrative and can be substituted with any device or mechanism which allows introduction of the liquid or gaseous sample. The sensor also includes a light source 150 and a detector 155. The substrate and the sample may be contained within a chamber.

The light source used in the sensor can be any suitable light emitting device which can emit light to illuminate the sample and the substrate. Examples of such suitable light emitting devices include semiconductor lasers, deuterium lamps, tungsten filaments, incandescent bulbs, fluorescent bulbs, neon light tubes, vapor lamps, light emitting diodes (LEDs) etc. In some embodiments, the light source may emit ultraviolet light, visible light, near infrared light, infrared light, or far infrared light. In illustrative embodiments, the light source may emit visible light. In some embodiments, the light source may emit radiation of a wavelength in the ultraviolet, visible, or near-, mid-, or far-infrared region of the spectrum. In some embodiments, the radiation includes ultraviolet radiation of a wavelength from 0.2 μm to 0.4 μm. In some embodiments, the radiation includes visible radiation of a wavelength from 0.4 μm to 0.75 μm. In some embodiments, the radiation may include radiation of a wavelength from 0.001 μm to 1000 μm. In other embodiments, the radiation includes near-infrared radiation having a wavelength from 0.75 μm to 2.5 μm. In another embodiment, the radiation includes mid-infrared radiation having a wavelength from 2.5 μm to 25 μm. In yet another embodiment, the radiation includes far-infrared radiation having a wavelength from 10 μm to 1000 μm. In illustrative embodiments, visible light can be used. In such embodiments, the wave length of the light may range from 300 nm to 1000 nm, 300 nm to 700 nm, and the like. Where a single wavelength is used for illumination, e.g. where a laser is the light source, some suitable wavelengths may include, but are not limited to 940 nm, 780 nm, 660 nm, 589 nm, 468 nm, 440 nm, 405 nm and the like. In some embodiments, visible to near infrared emission spectra by ultraviolet to visible light excitation may also be used.

Detectors for detecting a spectral profile are well known in the art. For example, such detectors include those for detecting far-infrared sources, infrared sources, near infrared sources, and ultra-violet-visible sources. The only limitation on the detector is that it be configured to detect light from the particular light source used, and any light transmitted through, or emitted by, a sample.

In some embodiments, the substrate material is such that it permits light from the light source to pass through without substantial deflection or scattering. In other embodiments, the substrate is such that it does not absorb infrared, ultraviolet or visible light absorbance at a monitored wavelength, or absorbs one or more of these at a wavelength that does not interfere with the spectral region that is to be monitored. In some embodiments, the substrate may be transparent. In other embodiments, the substrate may be made of suitable materials which permit the transmission of light emitted by light source, such as those described above.

The metalloporphyrin may be composed of various metals and porphyrin derivatives as discussed in various embodiments above. The metalloporphyrin may include a microbead or microcapsule and in a deoxygenated state by methods disclosed above. In other embodiments, the metalloporphyrin may be retained by a clathrate complex as disclosed above. In some embodiments, the metalloporphyrin includes microcapsules configured to absorb oxygen from the sample.

Figure 4:
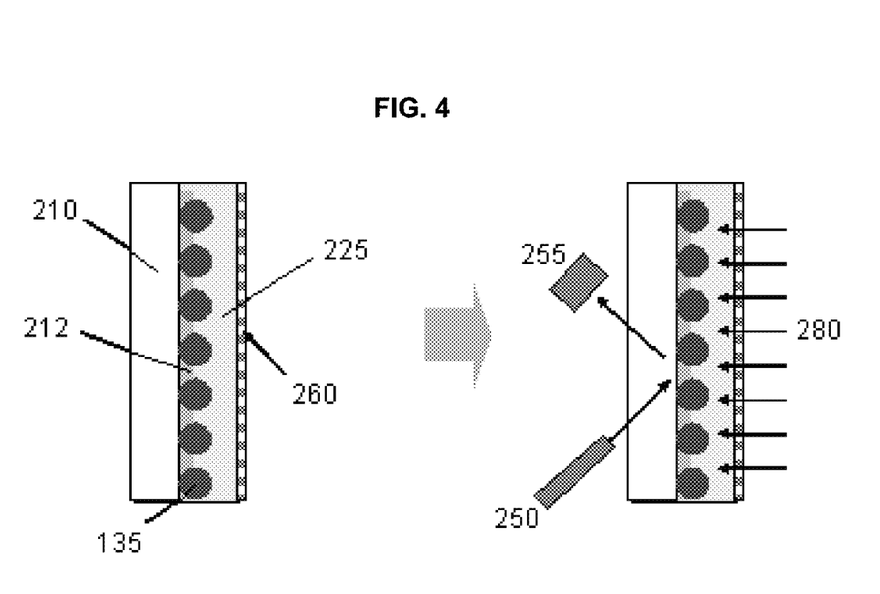
FIG. 4 is an illustration of an oxygen sensor for detecting oxygen in gaseous samples, and having an oxygen permeable membrane, according to some embodiments.

In various embodiments, the substrate may be configured to allow for the sample to be in contact with the metalloporphyrin. As described above, the sample may include a liquid phase or gaseous phase. Thus, the substrate may be configured in such a way that it allows the liquid or gaseous sample to be in contact with the metalloporphyrin to permit analysis. In some embodiments, the liquid samples can be directly introduced in to the substrate which is at least partially coated with metalloporphyrin. In some embodiments, the substrate may include an inlet from which liquid or gaseous samples can be introduced. In some embodiments, the substrate may further include an gas-permeable membrane, as described above, to permit the passage of gaseous samples containing oxygen. Such an embodiment is illustrated in FIG. 4. As seen from the illustration, the oxygen sensor includes an oxygen permeable membrane 260 and a substrate 210 coated with metalloporphyrin microcapsules 135 maintained in a deoxygenated state using deoxygenated water or carbon dioxide saturated water 225. The gaseous sample 280 to be detected can be introduced through the oxygen permeable membrane 260. The sensor also includes a light source 250 and a detector 255. To prevent air from prematurely passing through the permeable membrane 260, a cover or septum that is gas impermeable may be placed over or around the permeable membrane 260. The cover or septum may then be removed to measure the oxygen content of a sample.

In some embodiments, the substrate is at least partially coated with metalloporphyrins. Various metals and different porphyrin derivatives as those described above can be used. In some embodiments, the metalloporphyrin may include microcapsules or microbeads. In other embodiments, the metalloporphyrin is configured to absorb oxygen from the sample.

The light transmitted by the substrate can be detected by a detector configured to receive light from the substrate. A variety of detectors may be used depending on the type of light radiation to be detected. Thus, in some embodiments, UV detectors, IR detectors, UV/IR detectors, IR/IR detectors, and UV/Visible detectors can be used. In some embodiments, the detector is configured to detect an oxygen content of the sample by detecting a spectral profile. In some embodiments, the spectral profile is an emission spectrum or an absorption spectrum.

In another aspect, a method is provided for detecting oxygen gas or dissolved oxygen gas in a sample. In one embodiment, the method includes: introducing the sample to an oxygen sensor including a chamber which includes a substrate at least partially coated with a metalloporphyrin; a light source; and a detector; contacting the metalloporphyrin with the sample; illuminating the chamber and sample with the light source; and detecting a spectral profile of the light source before and after introducing the sample. Thus, light from the light source is passed through a sample to a detector and the spectral distribution of absorption or the transmitted light is measured.

The methods of the present technology can be used to detect the presence and quantity of oxygen in any sample. The sample can be in liquid or gaseous form. The sample can be a chemical sample, a biological sample, an environmental sample, and the like. In some embodiments, the sample may be adjusted to a known concentration prior to analysis. In some embodiments, the sample may need to be filtered or purified so that the influence of suspended matter, fine particles and the like can be eliminated prior to spectral analysis. In illustrative embodiments, the sample can be e.g. a sample from waste water treatment plants, wine production process, bio-reactions, environmental water testing, hydrocarbon fuels, bio-fuels, blood, plasma and tissue samples etc.

In some embodiments, an oxygen sensor as described above is used in the method for detecting oxygen gas or dissolved oxygen gas in a sample. As discussed in the apparatus section above, the oxygen sensor includes a substrate at least partially coated with a metalloporphyrin, a light source and a detector.

The metalloporphyrin may be composed of various metals and porphyrin derivatives as discussed in various embodiments above. The metalloporphyrin may include a microbead or microcapsule or may be retained by a clathrate compound. In certain embodiments of the method, the metalloporphyrin is in a deoxygenated state prior to introducing the sample and at least a portion of the metalloporphyrin in the deoxygenated state is converted to an oxygenated state upon the binding of oxygen. The metalloporphyrin compound can be maintained in a deoxygenated state by common methods known in the art and described above such as photochemical or radiation chemical methods, or by using carbon dioxide or deoxygenated water. Thus, for e.g., the substrate coated with metalloporphyrin may be contacted with aqueous carbon dioxide solution or deoxygenated water prior to being contacted with the sample.

While not wishing to be bound by theory, it is believed that the metalloporphyrin compound, which is initially in a deoxygenated state, readily binds to the oxygen in the sample thereby changing its chemical structure. This change in chemical structure of the metalloporphyrin from a deoxygenated state to an oxygenated state causes a change in spectral properties, which can be used to detect the amount of oxygen in the sample. Accordingly, in some embodiments, the method further includes observing a change in the spectral profile of the chamber after introducing the sample. In some embodiments, the spectral profile is an absorption or emission spectrum.

As noted, a change in the spectral properties may signal the presence of oxygen in a sample, and the magnitude of those changes may indicate oxygen concentration in a sample. Additionally, standards may be set such that a known amount of oxygen produces a known spectral change of a given magnitude. Based upon the standards, calibration curves may then be determined for the amount of oxygen in a sample for a given metalloporphyrin. Calibration curves may then form the basis for the quantitative determination oxygen content in a sample. Thus, in one embodiment, the method includes: introducing the sample to an oxygen sensor including a substrate at least partially coated with a metalloporphyrin; a light source; and a detector; contacting the metalloporphyrin with the sample; illuminating the chamber and sample with the light source; detecting a spectral profile of the sample, and comparing the spectral profile to a predetermined calibration curve to determine the amount of oxygen present in the sample.

The oxygen sensor and apparatus described herein can determine the oxygen concentration using a calibration curve. A calibration curve is a graph that represents a proportional expression describing the relationship a concentration of a species in a sample and a spectral output of a detector. In this case, the species is oxygen in the sample. The horizontal X-axis represents the oxygen concentration in the sample gas, the vertical Y-axis represents the detector output signal. Standard samples with known oxygen concentration are prepared and contacted with the metalloporphyrin and the corresponding detector response is used to plot the calibration curve. A sample of an unknown oxygen concentration is then passed into the oxygen sensor and the detector output is noted. This detector signal is then used to determined the oxygen concentration using the calibration curve.

In another aspect, an method for detecting the oxygen gas or dissolved oxygen gas content of a sample is provided. In some embodiments, the method includes: contacting the sample and a metalloporphyrin in an oxygen sensor including a chamber; a light source; and a detector; illuminating the chamber and sample with the light source; and detecting a spectral profile of the sample; where the metalloporphyrin includes a microbead or microcapsule, or is retained in a clathrate compound. Accordingly, the presence of oxygen may be detected by the change in spectral properties as measured before and after contact of the same and the metalloporphyrin, or the concentration of oxygen may be determined by reference to a calibration curve relating the spectral properties to samples of a known oxygen concentration.

The oxygen sensor including a chamber may be designed as disclosed hereinabove. In some embodiments, the sample to be detected may be introduced in the chamber followed by the metalloporphyrin in a deoxygenated state. In other embodiments, the metalloporphyrin in the deoxygenated state may be introduced in the chamber followed by the sample to be detected. After contacting the sample and the metalloporphyrin in the chamber, the chamber may be illuminated with the light source from the sensor. The spectral profile of the sample may be detected using the detector. Accordingly, the presence of oxygen may be detected by the change in spectral properties as measured before and after contact of the same and the metalloporphyrin, or the concentration of oxygen may be determined by reference to a calibration curve relating the spectral properties to samples of a known oxygen concentration.

As an illustrative example of a device according to one embodiment, a glass chamber and substrate may be used have dimensions of 10 cm×5 cm×2 cm. To this coupled a UV-VIS spectrometer with a tungsten halogen light source. To calibrate the device, deoxygenated hemoglobin microcapsules are added to the chamber and the absorbance is measured at 660 nm and 940 nm. A sample (0.1 ml) is then introduced into the chamber with the microcapsules and the absorbance is again measured at 660 nm and 940 nm. From the difference in the absorption at these two wavelengths the amount of oxygen in the sample may be determined.

Hemoglobin microcapsules of the illustrative example may be prepared according to the method described in *American Journal of Pathology* 159 (3) 1079-1088 (2001). The samples of the illustrative example may be a solution having a known concentration when preparing calibration curves, or unknown samples may be of any sources such as water from a river, lake, or other source, or solvents that contain oxygen.

The embodiments, illustratively described herein may suitably be practiced in the absence of any element or elements, limitation or limitations, not specifically disclosed herein. Thus, for example, the terms "including," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

EQUIVALENTS

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference in their entireties and for all purposes to the same extent as if each individual publication, patent, or patent application was specifically and individually incorporated by reference in its entirety for all purposes.

What is claimed is:

1. An oxygen sensing apparatus comprising:
    a substrate configured for spectral analysis, the substrate comprising at least a partial coating of a metalloporphyrin that is configured to bind oxygen;
    a light source configured to illuminate the substrate; and
    a detector configured to detect an emission spectrum or an absorption spectrum from the substrate;
    wherein:
        the metalloporphyrin comprises a microbead or microcapsule; and
        the porphyrin of the metalloporphyrin comprises, hemerythrin, chlorocruorin, vanabin, pinnaglobin, myoglobin, erythrocruorin, neuroglobin, leghemoglobin, cytoglobin, or a mixture of any two or more thereof.

2. The oxygen sensing apparatus of claim 1, wherein the metal of the metalloporphyrin is iron, vanadium, manganese, cobalt, nickel, copper, chromium, platinum, palladium, silver, or gold.

3. The oxygen sensing apparatus of claim 1, wherein the substrate comprises a chamber, a tube, or a channel.

4. The oxygen sensing apparatus of claim 1, wherein the substrate comprises quartz, glass, plastic, or a salt.

5. The oxygen sensing apparatus of claim 1, wherein the substrate is a salt comprising $CaF_2$ or $MgF_2$.

6. The oxygen sensing apparatus of claim 1 further comprising an gas-permeable membrane.

7. An oxygen sensing apparatus comprising:
    a chamber configured to permit spectral analysis;
    a metalloporphyrin configured to bind oxygen and encapsulated within a microbead or microcapsule;
    a light source configured to illuminate the chamber; and
    a detector configured to detect an emission spectrum or an absorption spectrum from the chamber;
    wherein:
        the metalloporphyrin is contained within the chamber during spectral analysis; and
        the porphyrin of the metalloporphyrin comprises hemerythrin, chlorocruorin, vanabin, pinnaglobin, myoglobin, erythrocruorin, neuroglobin, leghemoglobin, cytoglobin, or a mixture of any two or more thereof.

8. The oxygen sensing apparatus of claim 7, wherein the metal of the metalloporphyrin is iron, vanadium, manganese, cobalt, nickel, copper, chromium, platinum, palladium, silver, or gold.

9. The oxygen sensing apparatus of claim 7, wherein the chamber is a salt comprising $CaF_2$ or $MgF_2$.

10. A method for detecting oxygen gas or dissolved oxygen gas in a sample, the method comprising:

introducing the sample to an oxygen sensing apparatus comprising:
a chamber comprising a substrate at least partially coated with a metalloporphyrin configured to bind oxygen;
a light source configured to illuminate the chamber; and
a detector configured to detect an emission spectrum or an absorption spectrum from the chamber;
contacting the metalloporphyrin with the sample;
illuminating the chamber and sample with the light source; and
detecting an emission spectrum or an absorption spectrum before and after introducing the sample;
wherein:
the chamber is configured to permit spectral analysis;
the metalloporphyrin is encapsulated within a microbead or microcapsule;
the metalloporphyrin is contained within the chamber during spectral analysis; and
the porphyrin of the metalloporphyrin comprises hemerythrin, chlorocruorin, vanabin, pinnaglobin, myoglobin, erythrocruorin, neuroglobin, leghemoglobin, cytoglobin, or a mixture of any two or more thereof.

11. A method for detecting the oxygen gas or dissolved oxygen gas content of a sample, the method comprising:
contacting the sample and a metalloporphyrin configured to bind oxygen in an oxygen sensing apparatus comprising:
a chamber configured to permit spectral analysis;
a light source configured to illuminate the chamber; and
a detector configured to detect an emission spectrum or an absorption spectrum from the chamber;
illuminating the chamber and sample with the light source; and
detecting an emission spectrum or an absorption spectrum of the sample before and after introducing the sample;
wherein:
the metalloporphyrin is encapsulated within a microbead or microcapsule;
the metalloporphyrin is contained within the chamber during spectral analysis; and
the porphyrin of the metalloporphyrin comprises hemerythrin, chlorocruorin, vanabin, pinnaglobin, myoglobin, erythrocruorin, neuroglobin, leghemoglobin, cytoglobin, or a mixture of any two or more thereof.

12. The method of claim 10, wherein the metal of the metalloporphyrin is iron, vanadium, manganese, cobalt, nickel, copper, chromium, platinum, palladium, silver, or gold.

13. The method of claim 11, wherein the metal of the metalloporphyrin is iron, vanadium, manganese, cobalt, nickel, copper, chromium, platinum, palladium, silver, or gold.

* * * * *

UNITED STATES PATENT AND TRADEMARK OFFICE
CERTIFICATE OF CORRECTION

PATENT NO.        : 8,501,100 B2
APPLICATION NO.   : 13/000796
DATED             : August 6, 2013
INVENTOR(S)       : Fukui Page 1 of 1

It is certified that error appears in the above-identified patent and that said Letters Patent is hereby corrected as shown below:

On the Title Page, item (75), under "Inventor", in Column 1, Line 1, delete "Ohtsu" and insert -- Otsu --, therefor.

On the Title Page, item (56), under "OTHER PUBLICATIONS", in Column 2, Line 6, delete "Myglobin" and insert -- Myoglobin --, therefor.

In the Specifications:

In Column 2, Line 8, delete "an gas-permeable" and insert -- a gas-permeable --, therefor.

In Column 2, Line 32, delete "an gas-permeable" and insert -- a gas-permeable --, therefor.

In Column 2, Lines 40-41, delete "an gas-permeable" and insert -- a gas-permeable --, therefor.

In Column 4, Lines 29-30, delete "hemerithrin," and insert -- hemerythrin, --, therefor.

In Column 4, Lines 49, delete "state" and insert -- state. --, therefor.

In Column 8, Line 36, delete "an gas-permeable" and insert -- a gas-permeable --, therefor.

In the Claims:

In Column 12, Line 45, in Claim 6, delete "an gas-permeable" and insert -- a gas-permeable --, therefor.

Signed and Sealed this
Sixth Day of May, 2014

Michelle K. Lee
*Deputy Director of the United States Patent and Trademark Office*